US006444450B2

(12) United States Patent
Akkara et al.

(10) Patent No.: US 6,444,450 B2
(45) Date of Patent: *Sep. 3, 2002

(54) LARGE-SCALE PRODUCTION OF POLYPHENOLS OR POLYAROMATIC AMINES USING ENZYME-MEDIATED REACTIONS

(75) Inventors: Joseph A. Akkara, Holliston; Madhu S. R. Ayyagari, Brighton; David L. Kaplan, Stow, all of MA (US)

(73) Assignee: The United States of America as represented by the Secretary of the Army, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/014,522

(22) Filed: Jan. 28, 1998

(51) Int. Cl.⁷ ............... C12P 13/22; C12P 17/10; C12P 17/12; C12P 13/00; C12P 11/00
(52) U.S. Cl. .............. 435/108; 435/121; 435/122; 435/126; 435/128; 435/130; 435/156
(58) Field of Search ................ 435/122, 156, 435/128, 130, 126, 121, 108

(56) References Cited

U.S. PATENT DOCUMENTS

| 4,788,277 A | 11/1988 | Ibe et al. ............... 528/215 |
| 4,900,671 A | 2/1990 | Pokora et al. .......... 435/156 |
| 5,097,087 A | 3/1992 | Sanderson et al. ...... 585/255 |
| 5,153,298 A | 10/1992 | Pokora et al. .......... 528/86 |
| 5,210,173 A | 5/1993 | van Hout ............... 252/18 |
| 5,212,044 A | 5/1993 | Liang et al. ........... 430/192 |
| 5,278,055 A | 1/1994 | Cyrus et al. ........... 435/156 |
| 5,330,664 A | 7/1994 | Wollenberg et al. ..... 252/18 |
| 5,414,153 A | 5/1995 | Costantini et al. ...... 568/771 |

OTHER PUBLICATIONS

Kamat, S.V.; Iwaskewycz, B.; Beckman, E.J.; Russell, A.J., 90 Proc. Natl. Acad. Sci. USA 2940 (1993).
Y–P. Xu, G–L Huang and Y–T Ye, 47 Biotechnol. Bioeng. 117 (1995).
Ayyagari, M.S.; Marx, K.A.; Tripathy, S.K.; Akkara, J.A.; Kaplan, D.L., 28 Macromol., 5192–5197 (1995).
Ayyagari, M.; Akkara, J.A.; Kaplan, D.L., 47 Acta Polymer., 193–203 (1996).
Dorick, S.; Marletta, M.A.; Kilbanov, A.M.; 30 Biotechnol. Bioeng. 31 (1987).
Akkara, J.A.; Senecal; K.J.; Kaplan, D.L.; 29 J. Polm. Sci. A 1561 (1991).
Rao, A.M.; John, V.T.; Gonzalez, R.D.; Akkara, J.A.; Kaplan, D.L., 41 Biotechnol, Bioeng. 531 (1993).
Kurioka, H.; Komatsu, I.; Uyama, H.; Kobayashi, S., 15 Macromol. Rapid Commun. 507 (1994).
Ryu, K.; Stafford, D.R.; Dorick, J.S., 389 ACS Symp. Ser. 141 (1989).
Bruno, F.; Akkara, J.A.; Samuelson, L.A.; Kaplan, D.L.; Marx, K.A.; Tripathy, S.K., 5(5) J. Intel. Mat. Sys. Struct. 631 (1994).

*Primary Examiner*—Herbert J. Lilling
(74) *Attorney, Agent, or Firm*—Vincent J. Ranucci

(57) ABSTRACT

A process for large-scale, low cost, batch or continuous production of polyphenols using enzyme-mediated reactions and methods for recycling non-consumed reactants.

19 Claims, 13 Drawing Sheets

(a)

(b)

LARGE-SCALE PRODUCTION OF POLYPHENOLS OR POLYAROMATIC AMINES USING ENZYME-MEDIATED REACTIONS

The inivention described herein may be manufactured, used, and licensed by or for the U.S. Government for U.S. Government purposes without the payment to us of any royalty thereon.

FIELD OF INVENTION

A process for large-scale batch or continuous production of polyphenols using enzyme- mediated reactions where the reactions are carried out in 1) bulk solvents, 2) reversed micelles, or 3) a biphasic system. The process incorporates methods for recycling non-consumed reactants back into the system and controlling reaction conditions such that high product yields, control of molecular weight, and polydispersity are obtained.

BACKGROUND OF INVENTION

Phenolic resins such as novolacs and resoles are commercially produced by condensing phenol and formaldehyde at various molar ratios in the presence of acid or base catalysts. However, the confirmed carcinogenic nature of formaldehyde poses a major threat to personnel involved in polyphenol production in industry and to the end user. Residual amount of formaldehyde in the finished product is unavoidable and undesirable.

Alternatively, inorganic catalysts or biocatalysts can be used to produce polyphenols without the need for formaldehyde. Enzymatically synthesized polyphenols may find applications in coatings, laminates, wood composites, color developers, and recording materials. Such materials could be cast into thin films or fabric coatings. The polymers can also be tailored for applications in the detergent industry. In addition, polyphenols may be used in photolithography, rechargeable lightweight batteries, and electromagnetic shielding. Enzymatic polymerization of phenols and aromatic amines in mixtures of water-miscible solvents and water was first reported by Klibanov and co-workers, (J. S. Dordick, M. A. Marlett, A. M. Klibanov, *Biotechnol. Bioeng.* 1987, 30, 31–36.) and Pokora and Cyrus, (A. R. Pokora, W. L. Cyrus, U.S. Pat. No. 4,647,952, 1987, Mead Corporation., U.S.A.).

There are numerous advantages to using enzymes to catalyze phenol polymerization including mild reaction conditions, fast reaction rates, high substrate specificity and minimal by-product formation. Polymers produced by enzymatic reactions have the additional advantage of having extensive backbone conjugation leading to electronic and electro optic applications. Horseradish peroxidase (HRP) is the most commonly used enzyme for these polymerization reactions carried out in solvent/water mixtures and microemulsions.

Dordick et al., Vol. # 30,1987 *Biotechnol. Bioeng.* 31–36, used HRP in a dioxane/water system to prepare a number of polymers and copolymers from various phenolic monomers. Akkara et al., 29 *J. Polym. Sci. A* 1561 (1991), prepared polymers and copolymers of various phenols and aromatic amines using these same reactions and carried out detailed characterization of the polymer products. Para-alkylphenols were also polymerized at oil-water (reversed micelles) and air-water (Langmuir-Blodgett trough) interfaces. Because of their amphophilic nature, the alkylphenols are partitioned at the interface, and in the presence of HRP and hydrogen peroxide the monomers are oxidatively coupled to form polymers. The poly(para-alkylphenols) prepared in reverse micelles were shown to exhibit relatively more uniform molecular weight distribution than those prepared in bulk organic solvents.

However, earlier attempts to control the polymer molecular weight and molecular weight distribution by varying the time of reaction or hydrogen peroxide concentration were unsuccessful in both reversed micelles and bulk solvents. Initial hydrogen peroxide concentration was found to be stoichiometrically proportional to the monomer conversion, a hallmark of stepwise polymerization and a phenomenon observed previously, and there was no effect on the polymer molecular weight and polydispersity.

The polymers can be modified by adding functional groups to the polymeric backbone, significantly enhancing the utility of these polymers. "Functionalization" enables the polymers to be used to treat fabrics, to form selectively permeable membranes, and to improve the performance of integrated circuit chips, among other applications.

Palmitoyl chloride may be added to the polymer to make the polymer easily processable, e.g., as coatings, films, or finishes. Cinnamoyl chloride may be added to create controlled pore size membranes (e.g., "molecular sieves") or to enhance the polymers' ability to absorb UV radiation (e.g. photolithography, sunglasses, etc.). In their latter use, the modified polymers are applied to a silicon substrate as an undercoating (under non-functionalized polyphenols or polyaromatic amines that are then applied as a spin coating) in an IC chip to control the precision of UV etching, by inhibiting UV scattering, of circuitry into the spin-coated polymer layer. In addition, these cinnamoyl chloride-modified polymers are very thermostable, which allows their use in a variety of applications where heat is ordinarily a problem. In addition, photosensitive functional groups may be added to enhance the utility of the polymers in other applications.

The polymers also may be modified to create active matrices and systems allowing the controlled-release of materials, such as drugs, insecticides, and fertilizers. If biotin or other ligands are added to the polymer chain, the polymer can be used as chromatography packing, which may be used to separate and purify proteins.

Despite the study of how the functionality of the polymers varies depending upon whether, and with what, the molecules are modified, it has not been shown that the molecular weight and the molecular weight distribution (i.e. "polydispersity") of polyphenols and polyaromatic amines also can significantly influence the functional properties of the polymers.

Although the reactions employed by the invention are known in the industry, processes have not been developed for large-scale production of phenolic or aromatic amine polymers in enzyme-mediated reactions from which non-consumed reactants are recycled This invention relates to such a process for large-scale production of phenolic or aromatic amine polymers in enzyme-mediated reactions from which non-consumed reactants are recycled. The process specifically relates to recycling the solvent to minimize waste and lower processing costs.

SUMMARY OF INVENTION

It is therefore an object of this invention to provide a low cost process for large-scale production of polyphenols or polyaromatic amines using enzyme-mediated reactions from which non-consumed reactants are recycled back into the reaction system.

More particularly it is an object of this process to provide a closed system to recycle the solvent back into the reaction system to minimize waste and to lower processing costs.

It is a further object of this invention to provide a method for producing polyphenols or polyaromatic amines which incorporates methods for recycling non-consumed reactants and non-consumed reaction medium back into the system and for controlling reaction conditions such that high product yields, low molecular weight, and low polydispersity are obtained.

The process generally includes polymerizing a monomer in a reactor with various pre-reaction components, wherein polymerization is catalyzed by an enzyme, yielding phenolic or aromatic amine polymers, non-consumed reactants and reaction medium, wherein the non-consumed reactants and reaction medium form post-reaction components; isolating the polymers from the post-reaction components and recycling at least a portion of the post-reaction components back into a mixing unit.

The reactants comprise monomers, enzyme, and hydrogen peroxide. The reaction medium may be a reversed micellar solution comprising water, a solvent and a surfactant. The reaction medium may alternatively include water and a water-miscible solvent in a monophasic system. Additionally, in a biphasic system the reaction medium may comprise a first phase, where the first phase comprises water, and a second phase, where the second phase comprises a water-immiscible solvent. In this latter embodiment the reactor may comprise a stirred tank to create a dynamic emulsion.

After polymerization, the polymer may be isolated from the reaction components by means of a filtration unit yielding isolated polymers and a filtrate, where the filtrate includes the non-consumed reactants and the reaction medium.

After isolating the polymer, the recycling step may include the following steps.

(A) In a monophasic solvent system by: 1) isolating a sample of the filtrate; 2) analyzing the sample by means of a monitoring device to determine concentration of the non-consumed reactants and volume of the reaction medium, together comprising post-reaction components; 3) recycling the non-consumed reactants and reaction medium back into the system; 4) communicating the concentration and the volume levels for the post-reaction components to all flow controllers; and 5) introducing the calculated amounts of each reactant and reaction medium into the reactor by means of controlling the respective flow rate.

(B) In a reversed micellar solution by: 1) isolating a sample of the filtrate by means of a sampling port; 2) analyzing the sample by an analyzing means to determine the concentrations of nonconsumed reactants, surfactant and water and volume of the reaction medium, together the post-reaction components; 3) recycling the post-reaction components to a mixing unit via a feedback controller; 4) communicating the calculated concentrations and volume information from the feed back controller to the respective flow controllers; 5) introducing the calculated amounts of the reactants, surfactant, water and solvent into their respective mixing ports/units; 6) introducing the solution into the reactor; and 7) initiating the polymerization reaction by adding the calculated amount of hydrogen peroxide at a predetermined rate.

(C) In an immobilized system by: 1) analyzing the filtrate for nonconsumed reactants; and 2) returning the filtrate to the top of the bed after adding the calculated amounts of reactants and solvent.

BRIEF DESCRIPTION OF THE DRAWINGS

Other objects, features and advantages will occur to those skilled in the art from the following description of a preferred embodiment and the accompanying drawings in which.

DESCRIPTION OF THE PREFERRED EMBODIMENTS

Figure 1:
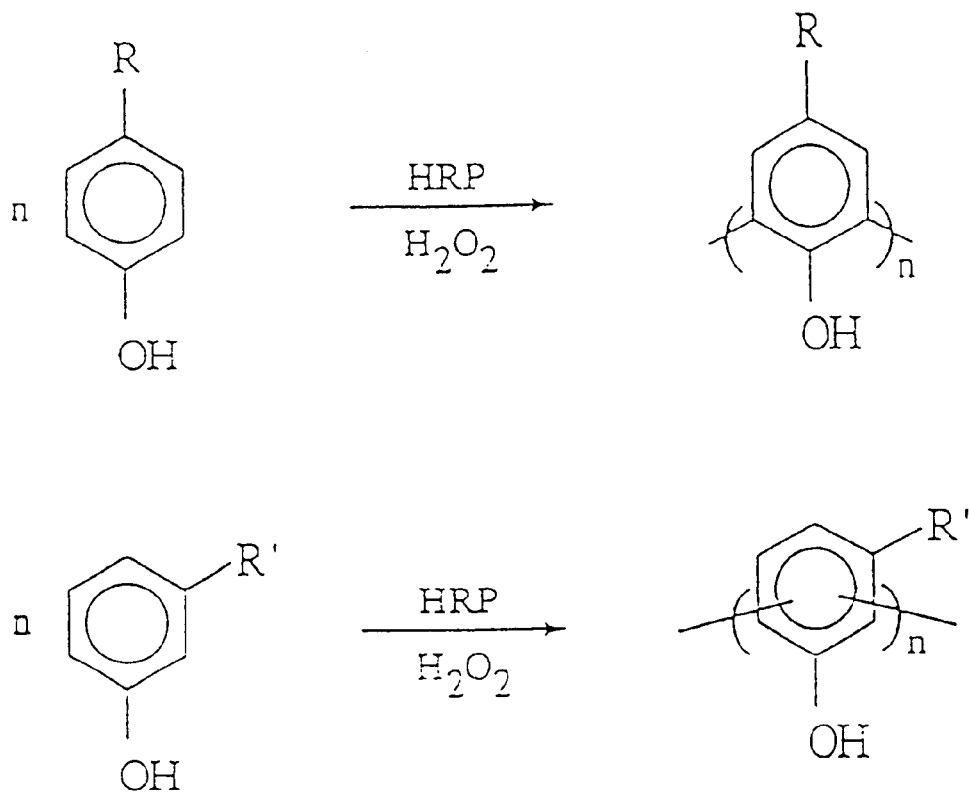
FIG. 1 is a schematic of meta- and para-substituted phenol polymerization catalyzed by horseradish peroxidase.

This invention relates to a process for large-scale production of phenolic or aromatic amine polymers where the non-consumed reaction components are recycled back into the system. The reactions utilize enzymes to catalyze polymerization and may be carried out in 1) bulk solvents, 2) reversed micelles, or 3) a biphasic system.

Free radical polymerization of p-ethylphenol and m-cresol, catalyzed by horseradish peroxidase, was carried out at ambient conditions in a number of organic solvent systems. While the dioctyl sodium sulfosuccinate/isooctane reversed micellar system afforded complete monomer conversion into polymer with an average molecular weight of 2,500, the addition of chloroform yielded lower molecular weights, with narrower distributions. Reactions carried out in dimethyl formamide produced mostly oligomers with uniform molecular weights. Poly(m-cresol) molecular weight could be controlled between 1,400 and 25,000 by appropriate design of the reaction medium comprised of ethanol-water mixture. Analysis of the polymers by GPC demonstrated the effect of LiBr on the molecular weights of poly(p-ethylphenol) and poly(p-phenylphenol). The polymers showed apparently high molecular weights with DMF as GPC solvent due to significant inter/intra-molecular associations. At 0.35% LiBr in DMF and above, these associations were eliminated to permit the estimation of true molecular weights. $^{13}$C-NMR and FTIR studies revealed that the repeat units in poly(p-ethylphenol) are primarily linked at ortho positions. The hydroxyl groups, which are not involved in bond formation, could be derivatized with palmitoyl and cinnamoyl chlorides.

EXAMPLE 1

A typical polymerization reaction was carried out in reversed micelles as follows. A 10 ml solution of 0.15 M dioctyl sodium sulfosuccinate (AOT) in isooctane was prepared, and 0.4 ml of an aqueous preparation of horseradish peroxidase (Type II) (12.5·M) was added to form a clear reversed micellar solution having a $W_o$ (molar ratio of water to surfactant) of about 15. Para-ethylphenol was added to the reversed micellar solution, and the polymerization reaction was initiated by adding drops of 30% hydrogen peroxide (w/w) (up to about 30% stoichiometric excess) while stirring the reaction mixture.

The reaction was exothermic with rapid formation of a yellowish precipitate. After continuing the stirring for several hours, the precipitate was centrifuged and washed repeatedly with pure isooctane to remove the surfactant and any unreacted monomer. The final precipitate was dried overnight under a reduced pressure at 50° C.

EXAMPLE 2

In cases where a mixture of chloroform and isooctane was used to form reversed micelles, the same procedure was followed except that the corresponding solvent mixture was used in place of isooctane. Dry isooctane and chloroform are used for these examples. These solvents are stored with molecular sieves to the solvents dry. However, stable (i.e., transparent and single-phase) reversed micellar solutions were found to be difficult to form with a mixture of chloroform and isooctane with 25% or less isooctane. A stable microemulsion could be obtained only up to a $W_o$ of 9 with 50% chloroform at room temperature, and phase separation occurred at higher values.

EXAMPLE 3

In the absence of reversed micelles, reaction mixtures were prepared by first dissolving the monomer and the enzyme in a mixture of HEPES (N-[2-Hydroxyethyl] piperazine-N'[2-ethanesulfonic acid]) buffer and solvent such as N,N-dimethylformamide (DMF). The reaction was initiated, as before, by the dropwise addition of hydrogen peroxide. The enzyme was completely soluble at 0.5 mg/ml concentration in DMF/water mixtures at all solvent compositions studied.

A. Structural Characterization

Figure 2:
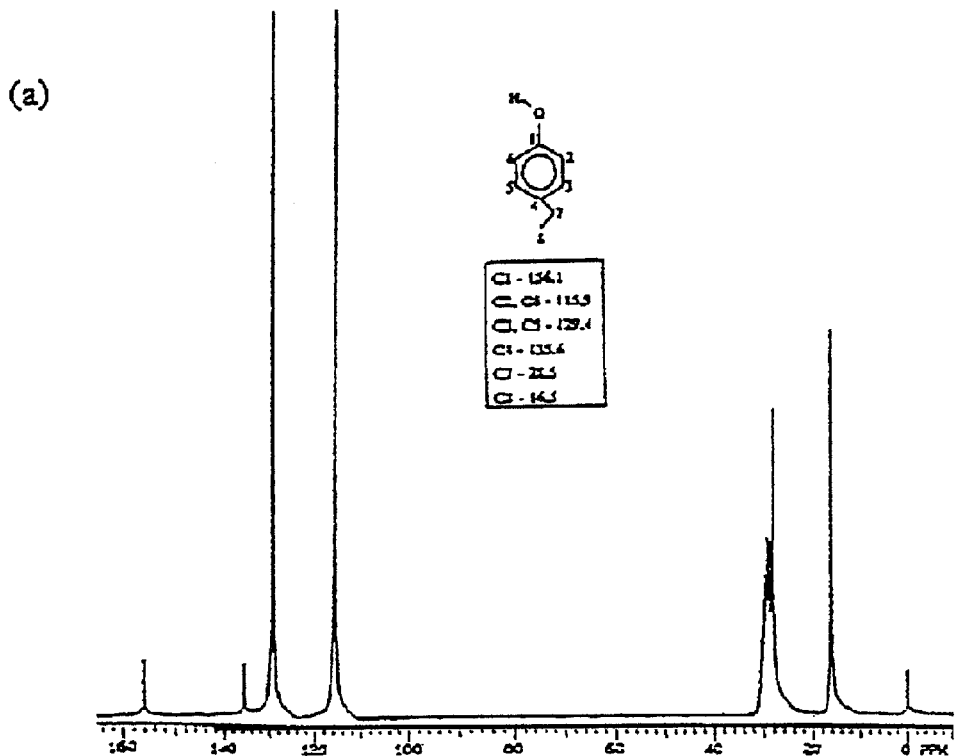
FIG. 2 is the $^{13}$C-NMR spectra for (a) p-ethylphenol and (b) poly(p-ethylphenol)
Figure 2:
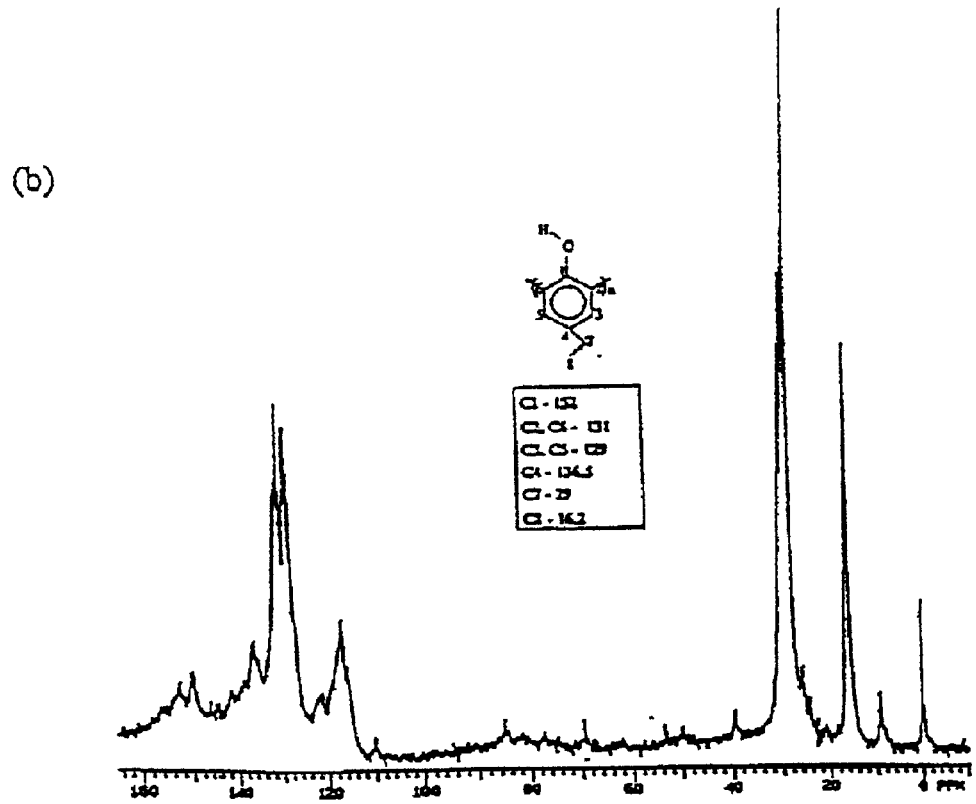

FIG. 1 illustrates the reaction scheme and the structures of monomers used. Crosslinking in polymer structure is expected in those cases where the ortho and para positions in the corresponding monomer structure are unsubstituted, as is the case with m-cresol. As shown in FIGS. 2a & 2b, $^{13}$C-NMR studies on poly(p-ethylphenol) indicate that the linkage between any two adjacent phenyl rings is largely at the ortho positions. However, this type of linkage may strain the polymer backbone in such a manner that the phenyl rings are out of plane with respect to the adjacent rings. As a result, the polymer backbone may be forced into a coiled structure.

$^{13}$C-NMR spectra on the monomer and polymer were recorded on a 200 MHz Varian instrument (C broad band probe, Model XL-200, Palo Alto, Calif.). Deuterated acetone and tetramethylsilane (TMS) were used as the solvent and the internal standard, respectively. Infrared spectra were recorded on a Perkin-Elmer 1760 FTIR-FTRaman spectrophotometer at 4 cm$^{-1}$ resolution. The samples were cast as thin films on a KBr window from chloroform solutions. UV spectroscopy studies were carried out on a Beckman DU 7500 spectrophotometer.

FIGS. 2a & 2b illustrate $^{13}$C-NMR spectra and peak assignments for the monomer and the polymer, respectively. The peak position at 131 ppm is in agreement with the theoretically calculated peak position for ortho linkages on the ring. On the other hand, if the monomer were linked at meta positions on the ring, the peaks for C3 and C5 should shift downfield from 129.4 ppm in the monomer to 144 ppm in the polymer. However, the polymer spectrum in FIG. 2b shows no such peak, therefore ruling out linkages at meta positions. There was no significant change in the peak position for C4, therefore ruling out ether linkages. Although the hydroxyl groups are involved in the formation of free radicals leading to polymer formation, they do not appear to be involved in bond formation. In addition, previous infrared studies revealed no ether linkage in the polymer structure. Thus the phenyl rings in the polymer appear to be linked primarily at ortho positions. The presence of free hydroxyl groups is also indicated by FTIR [see FIG. 6a(i) and 6b(i)].

B. Molecular Weight Determination

Molecular weights were determined on a Waters LC Module I instrument with an on-line GPC column (GBR mixed bed linear column with a molecular weight range of 100 to over 20 million). A UV detector at 270 nm was used to detect the polymer. The GPC data were collected and processed with Millennium GPC software supplied with the instrument. An eluent flow rate of 1 ml/min was maintained under isocratic conditions. Narrow molecular weight polystyrene standards were used for calibration. All samples were filtered through 0.2 micron PTFE filters, (Millipore, Bedford, Mass.), prior to injection. It was ascertained that the filters did not retain any polymer during filtration. The effects of LiBr in DMF on aggregation phenomena, as reflected by the weight average molecular weight of poly (p-ethylphenol), were also determined. LiBr is used to get true chromatographic separation based upon $M_w$ (LiBr breaks apart aggregated polymer molecules). A precise measure of $M_w$ is necessary to determine the functional utility of polymer.

For GPC analysis, poly(p-ethylphenol) was completely dissolved at a concentration of 1 mg/ml in a series of DMF-based solutions with varying LiBr concentrations in the range of 0 to 1% (w/v). A given composition (between 0 and 1% LiBr/DMF) of the GPC solvent was prepared by mixing pure DMF and 1% LiBr/DMF in appropriate proportions. For all injections, the composition of the GPC solvent and the solvent used to prepare the sample for injection were identical. A mixture of polystyrene standards ($M_w$, 122 to 2.7 million, narrow distribution with polydispersity in the range of 1.02 to 1.2) was prepared in all compositions of LiBr and DMF, and always injected before analyzing the polyphenol sample in the corresponding solvent.

Dimethylformamide is a good solvent for solution studies of polyphenols. Earlier reports used a mixture of DMF and methanol, at a ratio of 4 to 1, as a GPC solvent in the determination of molecular weights of polyphenols. DMF is an interesting solvent, especially for polyhydroxy compounds such as polysaccharides and polyphenols. For example, amylose is not soluble is DMF, but the polysaccharide swells as DMF penetrates into and 'wets' the polymer. However, it is well known that in the presence of about 3% (w/v) LiBr, amylose could be dissolved at a concentration of about 1% (w/v) in DMF. Polyphenol, like a polysaccharide, is also a polyhydroxy compound. Although DMF easily dissolves poly (p-ethylphenol), there still may be inter/intramolecular associations in the polymer. These interactions may result in an apparently high molecular weight in GPC analysis.

The potential aggregation of polyphenol molecules, and the use of a mixture of DMF and methanol to break the association, is known. Molecular weights in the range of a few hundreds to a few thousands have been reported for a number of different polyphenols, with poly(p-phenylphenol) exhibiting a molecular weight of 26,000. Using an identical GPC solvent composition, molecular weights of over 400,000 for poly(p-phenylphenol) prepared in a dioxane/water system have been reported. Similarly, an average molecular weight of about 20,000 with DMF/methanol solvent mixture as GPC eluent for poly(p-ethylphenol) prepared in AOT reversed micelles has been observed. However, it is not clear if the solvent mixture of DMF and methanol at 4:1 ratio is optimal to deaggregate the polymer chains and give a true molecular weight. To address this problem, the molecular weights of poly(p-ethylphenol) prepared in reversed micelles and dioxane/water system and poly(p-phenylphenol) prepared in dioxane/water system were analyzed as a function of LiBr concentration in DMF and DMF/methanol mixture as GPC eluents.

Figure 3:
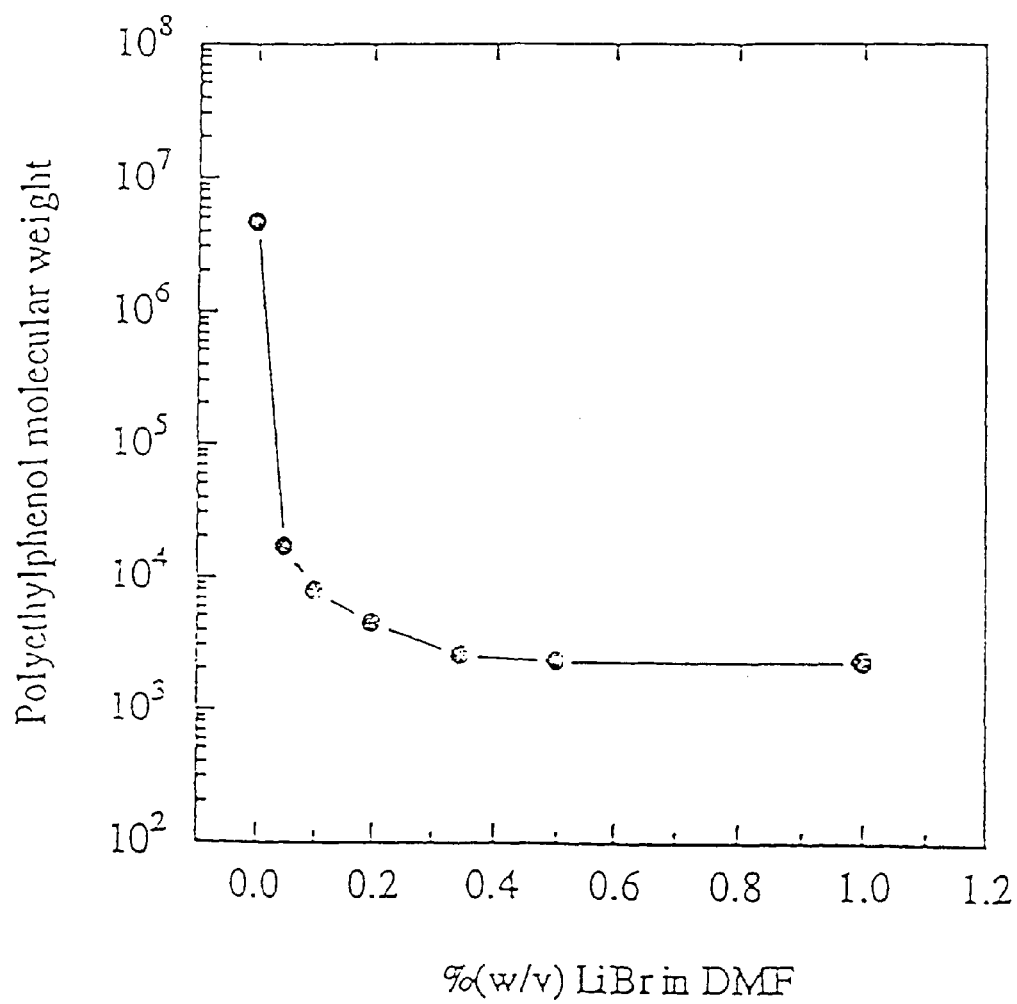
FIG. 3 is a graph of the effect of LiBr concentration in DMF on poly(p-ethylphenol) molecular weight.

FIG. 3 illustrates the effect of LiBr concentration in DMF as GPC eluent on the weight average molecular weight of poly(p-ethylphenol) prepared in reversed micelles. There is a dramatic decrease in the molecular weight by over three orders of magnitude when the LiBr concentration was increased from 0 to 0.35%. The molecular weight and dispersity of the polymer stabilized at about 2500 and 1.36, respectively, above 0.35% LiBr in DMF. Above this critical concentration of LiBr in DMF, there is no additional effect on the polymer a molecular weight.

An analogous phenomenon was observed with the solubility studies of amylose in DMF. Although DMF is capable of forming its own hydrogen bonds with the polysaccharide (as noted earlier, the polysaccharide swells in DMF, but is insoluble), it may not be able to completely disrupt the inter- and intramolecular forces. However, LiBr appears to be very effective in overcoming these inter- and intramolecular interactions. The polysaccharide becomes soluble at a concentration of 3% LiBr in DMF. It is possible that the solubility of the polyhydroxy compound is dictated by a fixed ratio between amylose and LiBr concentrations in DMF. The same argument applies to the molecular dissociation of poly(p-ethylphenol) in the presence of LiBr in DMF. Not unexpectedly, there was no effect of LiBr on the retention times of the polystyrene standards due to the lack of strong interchain interactions.

A mixture of DMF/methanol at 4:1 ratio was also used as the GPC solvent to determine the molecular weight of poly (p-ethylphenol) synthesized in AOT/isooctane reversed micelles. The result was a bimodal distribution with an average molecular weight of 90,000 and 300,000 for the two distributions. A similar bimodal molecular weight distribution was described by Akkara et al. for poly(p-phenylphenol). Molecular aggregation is still significant in this solvent system since the molecular weight of the sample dropped to about 2700 in the presence of 1% LiBr in DMF/methanol mixture at 4:1 ratio. Identical observations were made with a sample of poly(p-ethylphenol) synthesized in 85% dioxane/water system. Subsequently, a sample of poly(p-phenylphenol), synthesized in 85% dioxane/water, was analyzed for molecular weight both in DMF and DMF/methanol mixtures at different LiBr concentrations. As before, the polymer molecular weight dropped from well over 6 million to about 3400 on increasing LiBr concentration from 0 to 1% (w/v) in DMF. Similarly, poly(p-phenylphenol) showed a significant shift to lower molecular weight as the LiBr concentration in DMF/methanol mixture at 4:1 ratio was varied in the same concentration range as in DMF. In this case, the molecular weight dropped from about 500,000 to 3200. Table 1 lists the molecular weight and dispersity profiles of poly(p-ethylphenol) and poly(p-phenylphenol) synthesized under different conditions as a function of GPC solvent composition. Poly(p-ethylphenol) synthesized in reversed micelles exhibited a polydispersity of less than 1.4, and that prepared in bulk solvent, dioxane/water, >2. The average molecular weight of the polymer increased slightly as the surfactant concentration was increased, a phenomenon noted earlier.

TABLE 1

Molecular weight and dispersity profiles of poly(p-ethylphenol) and poly(p-phenylphenol) synthesized under different conditions as a function of GPC solvent composition

| Sample | Synthesis medium | $M_w(M_w/M_n)^1$ | | | |
|---|---|---|---|---|---|
| | | (a) | (b) | (c) | (d) |
| Poly(p-ethylphenol) | AOT/isooctane reserved micelles | >4.5M (<2.5) | 2500 (1.4) | 300,000 (>2.0) | 2700 (1.4) |
| Poly(p-ethylphenol) | 85/15 dioxane/water | >6.0M (>2.5) | 3400 (>2.0) | 500,000 (>2.0) | 3200 (>2.0) |
| Poly(p-phenylphenol) | 85/15 dioxane/water | >6.0M (>2.5) | 3000 (>2.0) | 300,000 (>2.0) | 3200 (>2.0) |

[1]Molecular weights ($M_w$) and dispersity ($M_w/M_n$) were determined with the following GPC solvents: (a) DMF; (b) 1% LiBr in DMF; (c) 4:1 DMF/methanol; and (d) 1% LiBr in 4:1 DMF/methanol.

C. Thermal Characterization

Figure 4A:
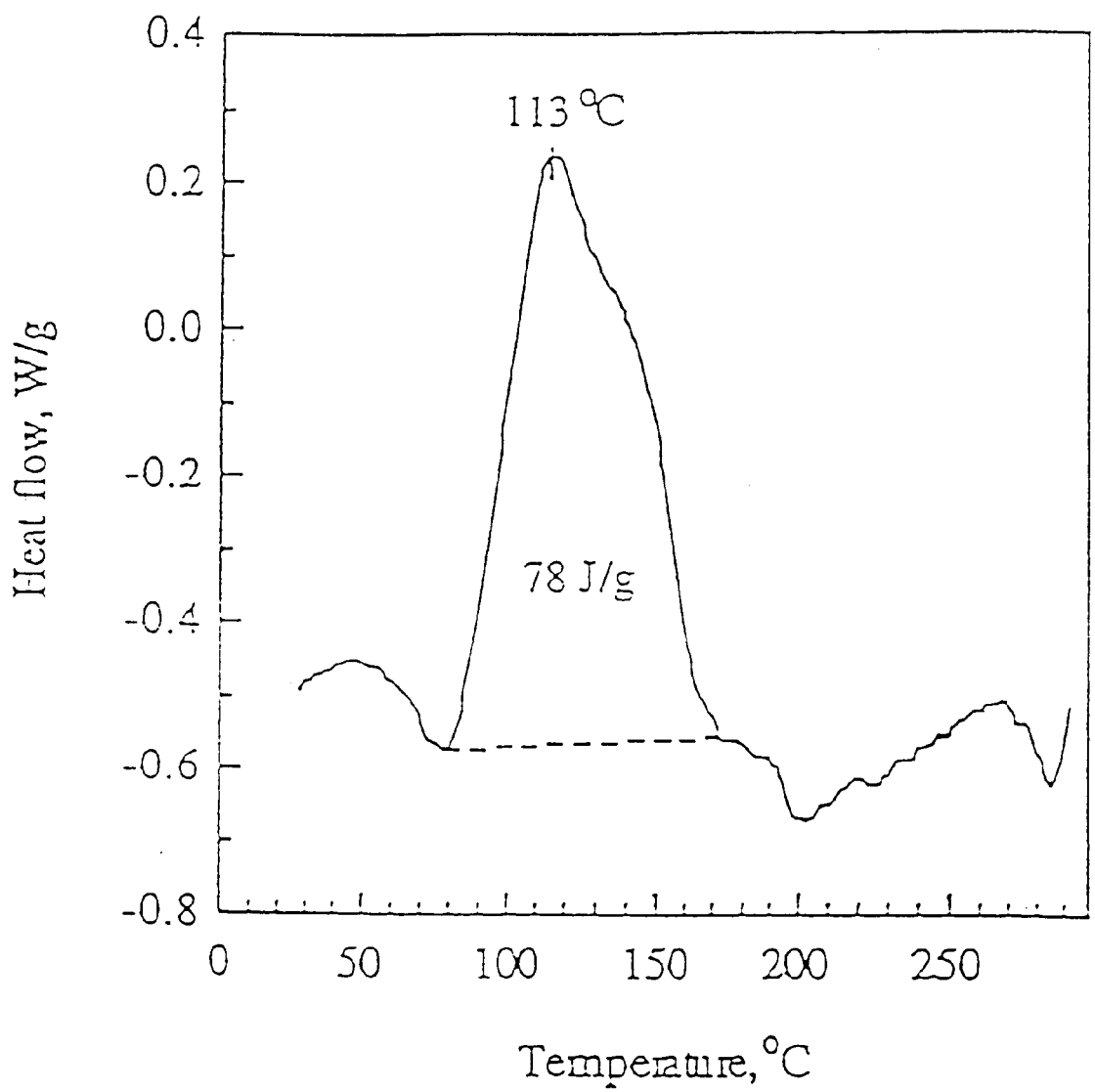
FIG. 4a is a differential scanning calorimetry (DSC) thermogram of poly(p-ethylphenol) prepared in reversed micelles.
Figure 4B:
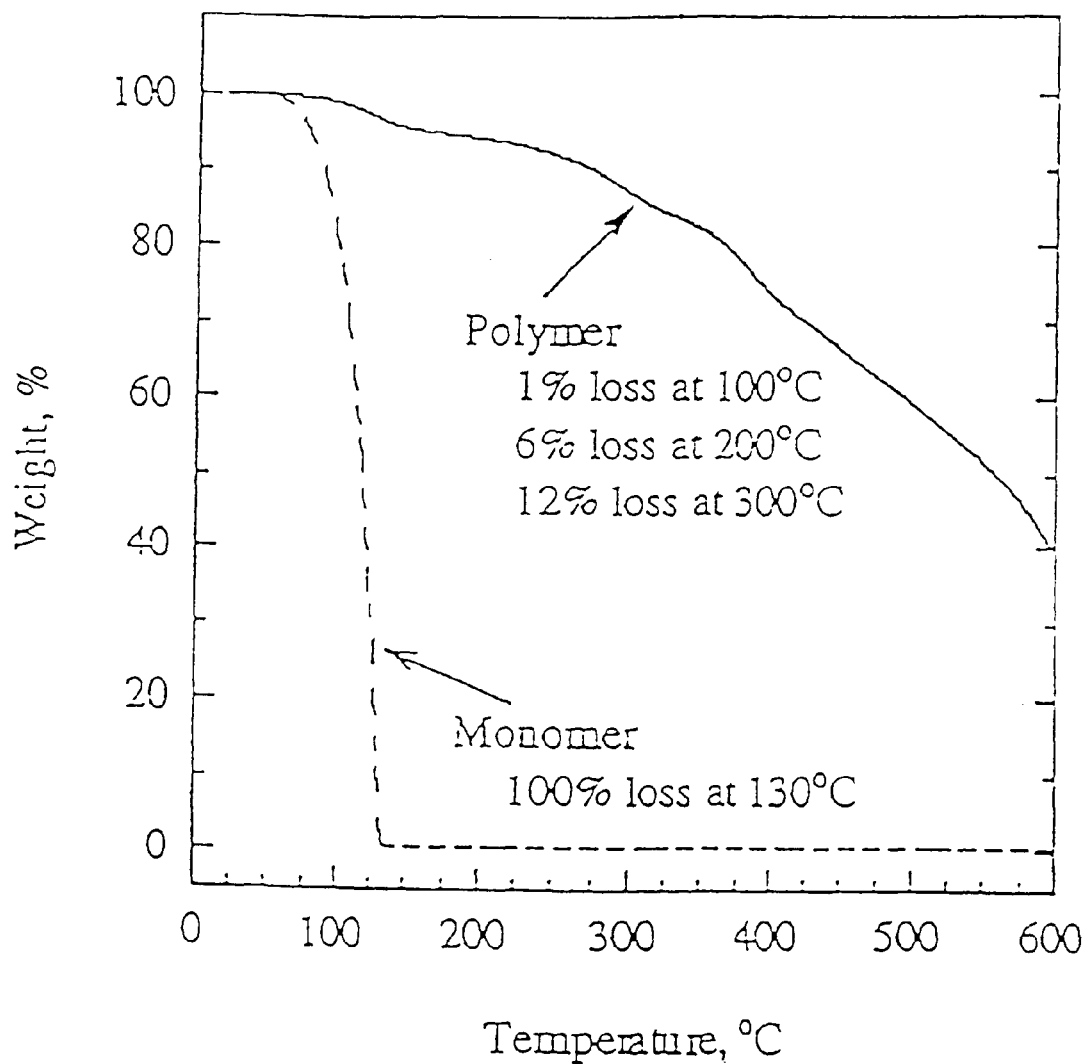
FIG. 4b is a thermogravimetric analysis (TGA) of p-ethylphenol and poly(p-ethylphenol) prepared in reversed micelles.

Thermal characterization of polymers was carried out on Du Pont thermal analyzers. For differential scanning calorimetry (DSC) analysis, the polymers were hermetically sealed, and heated under a nitrogen atmosphere at a temperature gradient of 10° C. per minute from room temperature to 300° C. Thermogravimetric analysis (TGA) was carried out at the same temperature gradient and under nitrogen atmosphere, but heated to 600° C. The thermal properties of p-ethylphenol and poly(p-ethylphenol) prepared in reversed micelles are illustrated as DSC and TGA thermograms in FIGS. 4a & 4b, respectively. The polymer was reasonably stable until a temperature of about 250° C., with a loss of less than 10% of the material (6% loss occurred before 200·c presumably in part due to loss of water). The exotherm at about 110° C. in the polymer DSC thermogram may be due to cross linking in the polymer or due to loss of heat of crystallization. Once heated over 200° C., the exotherm was irreversibly lost.

Figure 5:
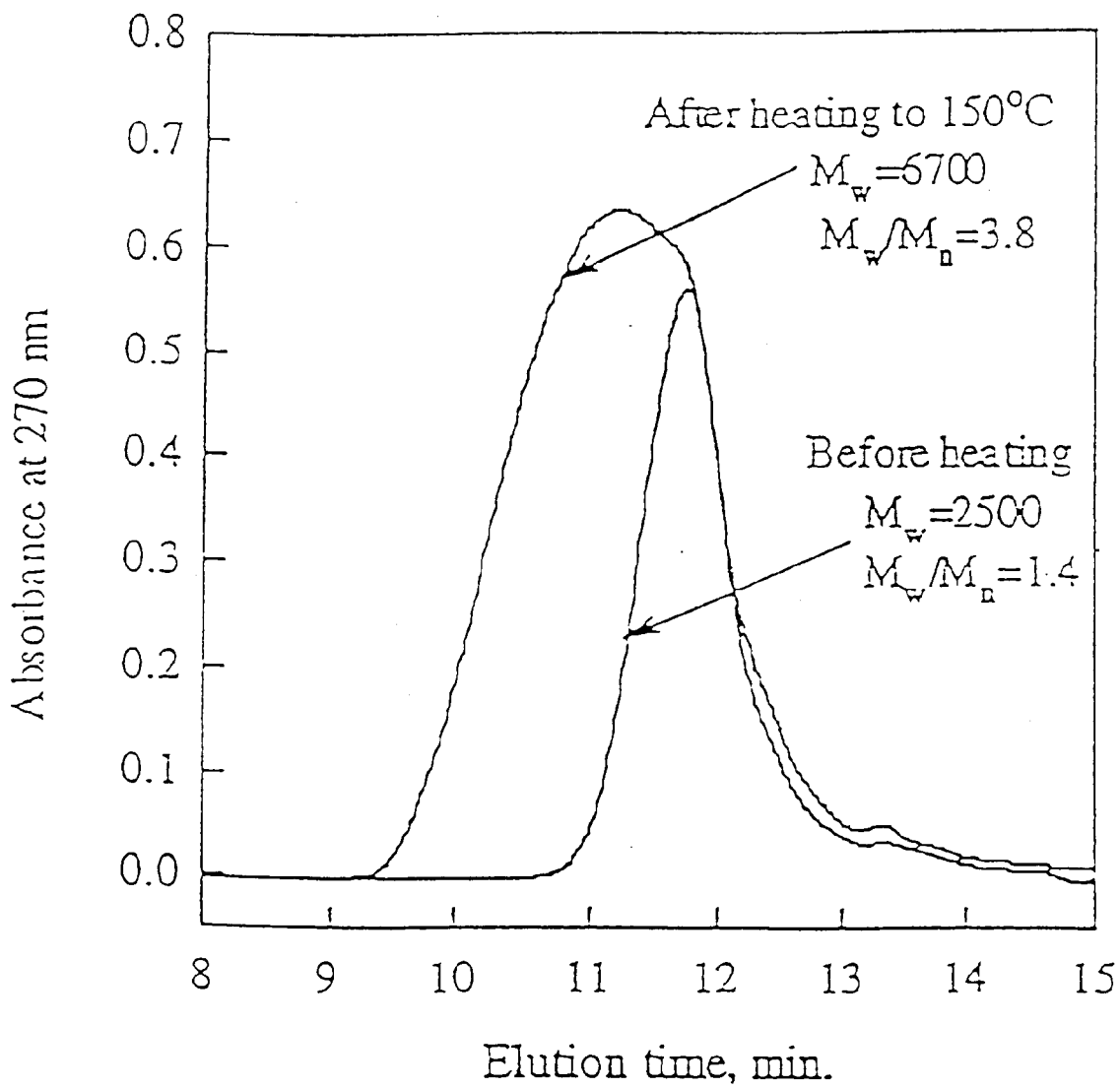
FIG. 5 shows the molecular weight distribution of poly (p-ethylphenol) before and after heating.

GPL analysis indicated a 170% increase in molecular weight, presumably due to cross-linking, when a sample of poly(p-ethylphenol) was heated to 150° C., and the polymer became significantly more polydisperse than the corresponding untreated polymer. FIG. 5 shows portions of the GPC profiles of poly(p-ethylphenol) before and after heating the polymer to 150° C. Both samples were easily soluble in 1% LiBr/DMF solution and this solution was also used as eluent. X-ray diffraction studies on the samples revealed a partial crystallization of the heat-treated polymer.

EXAMPLE 4

Phenol polymerization was carried out in a mixture of DMF and water at various ratios to investigate the solvent effect on enzyme activity and on the polymer molecular weight. The objective was to investigate if the molecular weight of polyphenols could be controlled, while maintaining a reasonably narrow molecular weight distribution, by varying reaction system parameters such as time of reaction, hydrogen peroxide concentration, and solvent composition. Table 2 sets forth the ranges of solubility parameters and dielectric constants covered by the solvent systems used for polymerization reactions.

TABLE 2

Ranges of solubility parameters and dielectric constants covered by the solvent systems used for polymerization reactions.

| Solvent systems | Solubility parameter (MPa½) | Dielectric constant |
|---|---|---|
| Isooctane/ | 14 | 2 |
| chloroform | 19 | 5 |
| DMF/ | 25 | 37 |
| water | 48 | 78 |
| 1,4-Dioxane/ | 20 | 30 |
| water | 48 | 78 |
| Ethanol/ | 26 | 24 |
| water | 48 | 78 |

The solvent mixtures, listed in Table 2, were selected on the basis of the range of solubility parameters that they cover. The wide variation in solubility parameters and dielectric constants for each system was similar to that found in certain supercritical fluids as a function of pressure. These properties not only influence the solubility of the growing polymer chain in the corresponding reaction medium, but significantly affect enzyme activity (solvents with high dielectric constants are known to denature the enzyme). However, unlike in supercritical fluids, the solvent properties can be varied at ambient conditions of pressure and temperature.

The reaction medium composition was varied from 100% DMF to 100% water. As before, the reaction was initiated with the addition of hydrogen peroxide at room temperature and with stirring. Interestingly, and analogous to the dioxane/water system, there was no sign of reaction (i.e., no heat or color generation) in the reaction mixtures containing 85% or more organic solvent, and the solutions remained clear throughout the addition of hydrogen peroxide. On the other hand, heat evolution (due to exothermic reaction) followed the reaction in solvents with 60% or less DMF, and the solutions became colored and opaque instantaneously.

It is clear that DMF sustained enzyme activity up to a concentration of 60%, although the presence of water was necessary. The monomer solubility in 20% DMF solution was poor, and solution turned into a stable emulsion prior to initiating the reaction. The reactions were continued for a few more hours before the solvent was evaporated under reduced pressure. The precipitates were washed with water and isooctane to remove buffer salt, the enzyme and any unreacted monomer. The dried precipitates were dissolved in 1% LiBr/DMF and their molecular weights were analyzed as described earlier. Table 3 shows the effect of solvent composition on the polymer molecular weight and dispersity (reactions in bulk and in the absence of reversed micelles).

TABLE 3

Effect of solvent composition on the polymer molecular weight and dispersity (reactions in the absence of reversed micelles).

| Synthesis medium | Monomer Conversion[1] | Polymer Yield | $M_w$ | $M_w/M_n$ | Comments |
|---|---|---|---|---|---|
| 100/0 DMF/water | 0% | 0% | | | no reaction |
| 85/15 DMF/water | 20% | 10% | 281 | 1.23 | dimers soluble in 85% DMF |
| 60/40 DMF/water | 80% | 75% | 612 | 1.20 | oligomers soluble in 60% DMF |
| 40/60 DMF/water | 80% | 80% | 675 | 1.05 | oligomers soluble in 40% DMF |
| 20/80 DMF/water | 75% | 75% | 658 | 1.02 | oligomers soluble in 20% DMF |
| 0/100 DMF/water | 50% | 35% | 400 | 1.90 | oligomers soluble in 100% DMF |
| 85/15 Dioxane/water | 80% | 15% | 3000 | 2.10 | Insoluble polymer soluble oligomers |

[1]Monomer converted/monomer added initially

The polymer yield, defined as a ratio of the amount of polymer recovered as an insoluble fraction in isooctane to the amount of monomer converted, was about 75% for cases where the DMF content in the reaction mixture was between 20% and 60%. Molecular weight analyses revealed that the polymers were in fact oligomers with an average molecular weight of about 650, (significantly lower than that obtained with the AOT/isooctane reversed micellar system), and a polydispersity of 1.03-1.20. The molecular weight was not variable with DMF content, indicating that either the solubility of growing chains during the reaction was not sustained by DMF/water (up to 60% DMF) or the enzyme became inactive.

Ethanol-HEPES buffer mixtures were also used to polymerize m- and p-cresol or p-ethylphenol in the study of molecular weight control. m-Cresol was studied in greater detail since it allows the study of a much broader molecular weight range than p-cresol or p-ethylphenol. Ethanol is a solvent of choice in view of its environmental compatibility and ease of regeneration. In addition, the enzyme is active in ethanol/buffer mixtures at levels up to at least 60% ethanol. Enzyme activity was studied as a function of ethanol content, and it was found that 20 to 40% ethanol was optimal for the conversion of about 50% monomer into polymer (20,000 molecular weight, degree of polymerization of 200). At an enzyme concentration of 2 mM, the conversion was essentially complete in about 10 minutes. Although there was no significant improvement in the monomer conversion when the reaction was continued for 24 hours, the molecular weight of poly(m-cresol) increased by about 75%. Table 4 shows the effect of ethanol content on monomer conversion and the molecular weight of poly(m-cresol) in ethanol/water systems. Ethanol appears to be a useful solvent when higher molecular weight polymer is desired. Replacing HEPES buffer with deionized water resulted in no noticeable change in reaction rates or in polymer properties.

TABLE 4

Effect of ethanol content on monomer conversion and the molecular
weight of poly(m-cresol) in ethanol/water systems
Polydispersity in all cases was >2.5
Unless noted otherwise, HRP concentration was 0.1 mg/ml.

| Solvent Composition | Monomer conversion | Polymer $M_w$ | Comments |
|---|---|---|---|
| 100% buffer | 40% | 2200 | polymer removed once at the end; 60% conversion possible when HRP and $H_2O_2$ added in pulses |
| 100% buffer with 1% KCl | 40% | 1400 | polymer removed as it formed; 60% conversion possible when HRP and $H_2O_2$ added in pulses |
| 80/20 water/EtOH | 90% | 22000 | $M_w$ of 6000 to 22000 possible at intermediate stages of reaction |
| 60/40 water/EtOH | 47% | 10000 | Lower molecular weights possible at intermediate stages of reaction |
| 40/60 water/EtOH | 11% | 3000 | 90% conversion & 24000 $M_w$ at 5X enzyme concentration |
| 20/80 water/EtOH | 3% | — | 20% conversion & 2000 $M_w$ at 5X enzyme concentration |
| 100% EtOH | 0% | | Insoluble enzyme |

Although high molecular weight polymers were produced with poly(m-cresol) due to crosslinking and with ethanol, in some applications, such as photoresists and detergent formulations, oligomers are desirable. Hence, m-cresol was polymerized in 100% buffer/water, and as a result, the polymer molecular weight decreased to 2,500. During the reaction the polymer molecular weight gradually increased without significant improvement in monomer conversion. It was therefore attempted to isolate the polymer as the polymerization process continued. This was achieved by carrying out the reaction in the presence of 0.5 to 1 (w/v)% KCl in the medium. While the salt, up to around 3% had no effect on the enzyme activity, it caused precipitation of the polymer as it formed. The polymer precipitate was isolated by filtration and the filtrate was returned to the reaction vessel. The enzyme in the filtrate was no longer active, therefore, enzyme and peroxide were added in pulses such that fresh enzyme was always available after each filtration to assure continued polymer formation. However, the rate of polymerization dropped as the reaction continued after each filtration in spite of the presence of significant amounts of the residual monomer, fresh enzyme, and hydrogen peroxide. The polymer yield was about 40% after completely adding all the enzyme and hydrogen peroxide to a final concentration of 2·M enzyme and 30% stoichiometric excess of the peroxide. The polymer molecular weight was about 1,400. Further polymerization was still possible in the remaining reaction mixture if fresh enzyme and peroxide were further added. Therefore, the polymerization process could be continued, in theory, until all monomer was consumed. When the polymer was not removed by filtration and the reaction was run with the identical additions of enzyme and hydrogen peroxide, the final polymer molecular weight was over 2,000. The polydispersity was about 2.5 in both cases of whether the polymer was removed intermittently or not.

It is thus possible to control the polymer molecular weight by manipulating the reaction and/or process conditions. In the case of poly(m-cresol), it is possible to obtain control of molecular weight from 1,400 to 25,000, with a polydispersity of about 2.5, by the selection of the reaction medium. Enzyme activity is a function of the reaction medium composition which influences monomer conversion. However, the polymer molecular weight is also strongly influenced by the polymer solubility and the length of time it is in contact with the enzyme and reacting species in the reaction mixture, even after precipitation.

In order to minimize the enzyme inactivation, a less polar solvent than DMF or ethanol was sought as the reaction medium. Accordingly, chloroform was used to carry out the phenol polymerization reaction. A mixture of chloroform and isooctane was used for the reactions, and the polarity of the medium was gradually varied by adding chloroform and thus changing the composition from 100% isooctane to 100% chloroform. However, the enzyme powder was poorly dispersed in this solvent system, and it became necessary to prepare AOT reversed micelles with the chloroform/isooctane mixture, as described earlier. As the isooctane content in the reaction mixture was lowered from 100%, the polymer yield dropped from 100% (in pure isooctane reversed micelles) to about 10% (in pure chloroform reversed micelles) These results are shown in Table 5.

TABLE 5

Effect of solvent composition on the polymer molecular weight
and dispersity (reactions in the AOT reversed micelles)
using isooctane and chloroform.

| Synthesis medium | Monomer Conversion | Polymer Yield | $M_w$ | $M_w/M_n$ | Comments |
|---|---|---|---|---|---|
| 100% Isooctane | 100% | 100% | 2500 | 1.36 | $W_0 = 15$ |
| 100% Isooctance | 90% | 100% | 2500 | 1.38 | $W_0 = 9$ |
| 75/25 Isooctane/$CHCL_3$ | 100% | 85% | 1681 | 1.53 | $W_0 = 9$ |
| 50/50 Isooctane/$CHCl_3$ | 100% | 75% | 3461 | 1.85 | $W_0 = 9$ |
| 25/75 Isooctane/$CHCl_3$ | 75% | 35% | 3601 | 1.83 | $W_0 = 9$ phase separation |
| 100% $CKCl_3$ | 20% | 10% | 1000 | 1.07 | $W_0 = 9$ phase separation |

Polymer molecular weight was maximum in 50–75% chloroform in isooctane with a polydispersity of 1.5 to 1.9. However, the polymer exhibited a low polydispersity of 1.07 in 100% chloroform. The poor polymer yields at high chloroform contents are perhaps due to the formation of unstable microemulsion systems leading to phase separation. As a result, the contact between the enzyme and the monomer is inefficient and the polymer yield is poor. Smaller $W_o$ values also contribute to poor monomer conversion. One approach is to eliminate the surfactant altogether by polymerizing phenolic monomers in a biphasic system where large amount of water containing enzyme is mechanically dispersed in a hydrophobic organic solvent containing the monomer. Preliminary results indicate that a number of polymers including poly(p-ethylphenol) of molecular weight 2500 can be prepared in chloroform/buffer (50:50 v/v) or an isooctane/water (50/50) biphasic system.

The hydroxyl groups in enzymatically prepared polyphenols do not a participate in bond formation, as noted earlier from $^{13}C$-NMR studies. The FTIR spectrum of the polymer, shown in FIGS. 6a(i) and 6b(i), also illustrates the point with a broad peak at 3400 cm$^{-1}$ due to 0-H stretch. Thus the hydroxyls on the polymer are available for chemical modifications such as esterification. Esterification was carried out in chloroform with palmitoyl and cinnamoyl chlorides in the presence of stoichiometric amount of pyridine to scavenge HCl produced in the reaction.

Figure 6A:
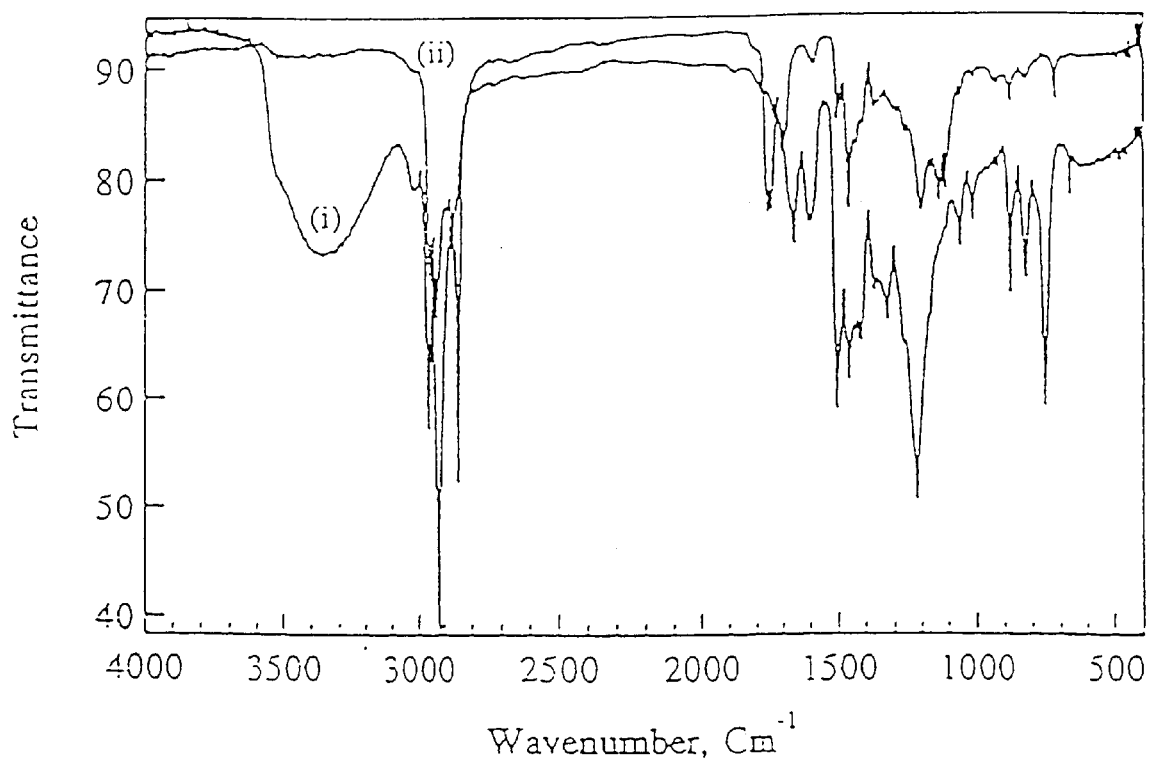
FIG. 6a shows FTIR spectra of poly(p-ethylphenol) (i) before and (ii) after esterification with palmitoyl chloride.
Figure 6B:
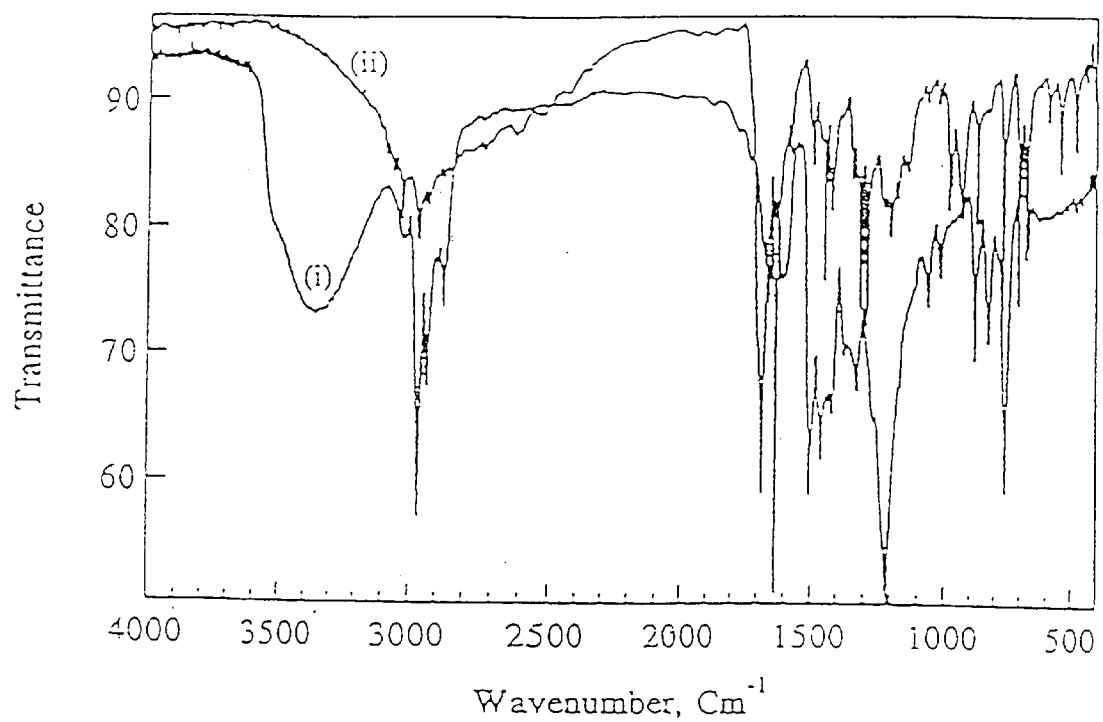
FIG. 6b shows FTIR spectra of poly(p-ethylphenol) (i) before and (ii) after esterification with cinnamoyl chloride.

FIGS. 6a and 6b illustrate FTIR spectra of poly(p-ethylphenol) before and after functionalization with palmitoyl and cinnamoyl moieties, respectively, at the hydroxyl groups of the polymer. FIG. 6a shows the presence of alkyl chains in the polymer due to palmitoyl groups, confirmed by the presence of strong peaks between 2800 and 3000 cm$^{-1}$ due to asymmetric and symmetric C—H stretch in methyl and methylene groups of the alkyl chains.

Figure 7:
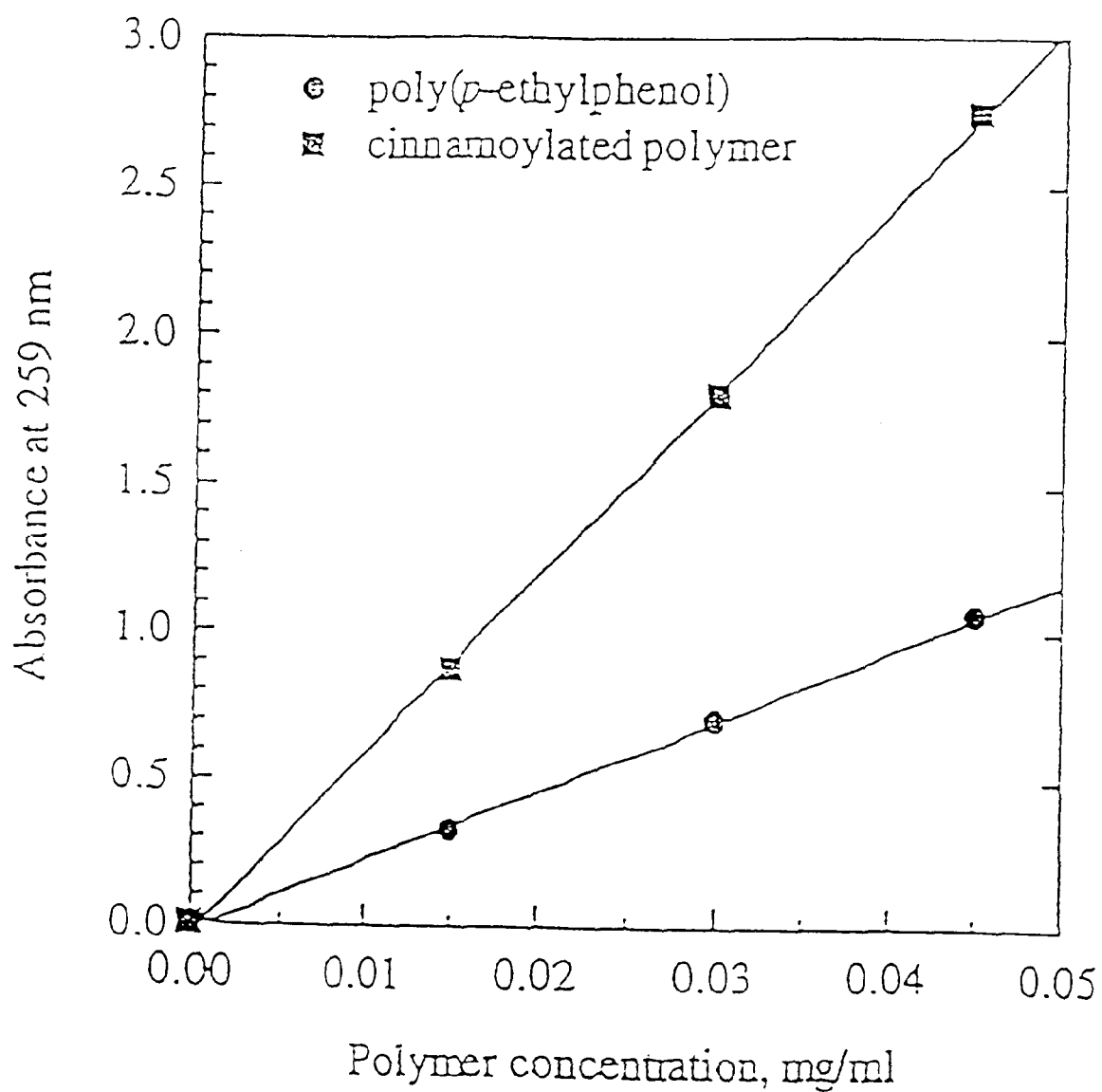
FIG. 7 shows the UV absorbance at 259 nm of poly (p-ethylphenol) before and after cinnamoylation.

In addition, the peak for 0-H stretch at 3400 cm$^{-1}$ disappeared in the esterified polymer indicating the participation of the hydroxyl groups in the reaction. The ester formation was also confirmed by the presence of C=O stretch at 1750 cm$^{-1}$ in the modified polymer. Similarly, cinnamoylation of the polymer was confirmed by the disappearance of 0-H stretch as well as from the strong presence of C=C ring stretch at 1600 cm$^{-1}$, shown in FIG. 6b. UV spectroscopic studies, carried out with acetonitrile solutions of the polymer, showed an increased absorbance for the cinnamoylated polymer at 259 nm due to the presence of additional phenyl ring, as shown in FIG. 7.

Figure 8:
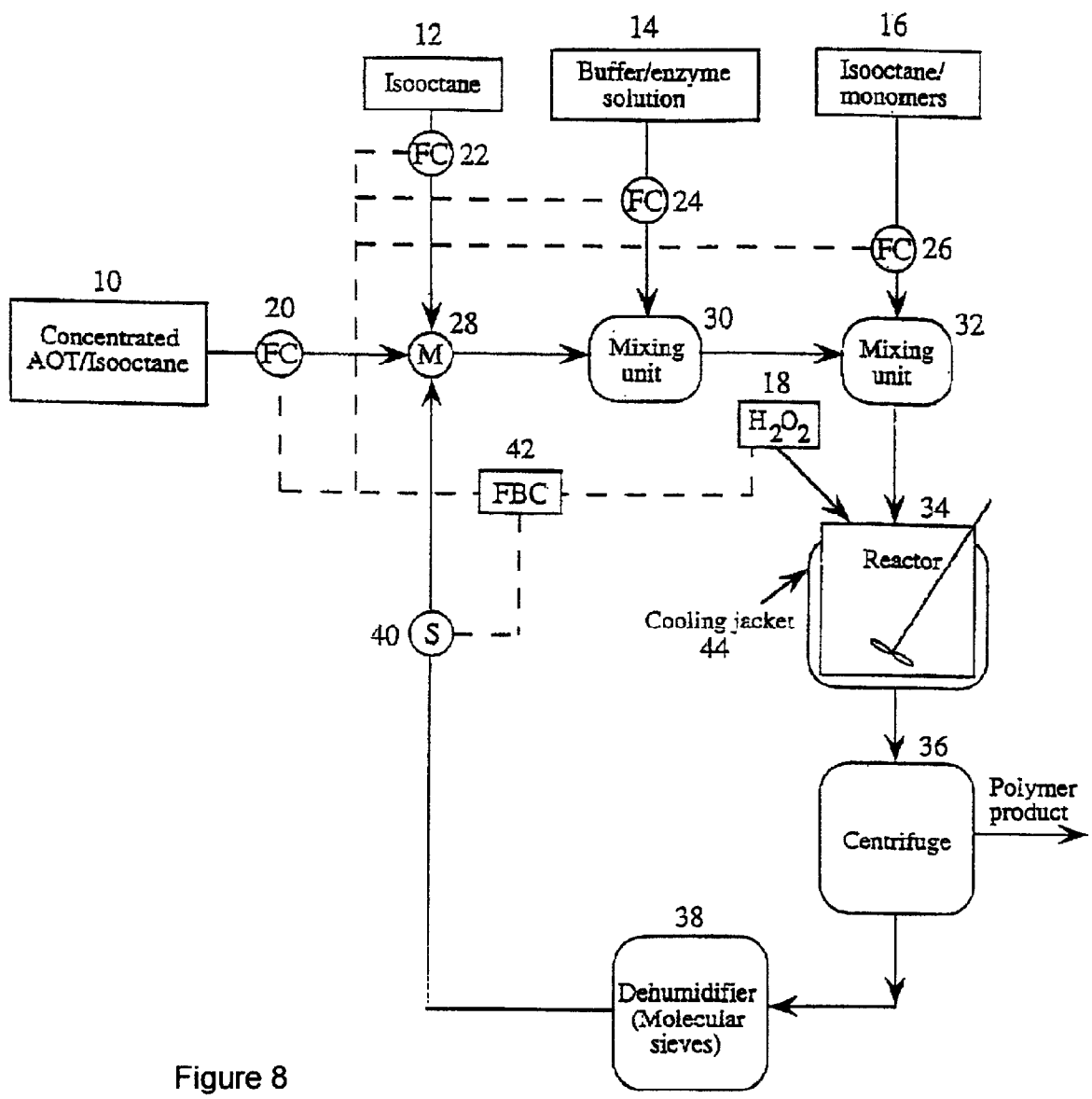
FIG. 8 is a schematic drawing of a preferred embodiment of the invention.

A preferred embodiment, shown in FIG. 8, comprises polymerizing a monomer by horseradish peroxidase (HRP) at the oil-water interface of water-in-oil microemulsions (reversed micelles). FIG. 1 is a schematic of meta- and para-substituted phenol polymerization catalyzed by HRP. The side chains do not participate in the reaction, but they have an effect on polymer properties, i.e. the position of the polymer link depends on the position of the side chain.

FIG. 8 is a schematic diagram of enzymatic polyphenol synthesis in reversed micelles. For example, p-ethylphenol could be polymerized in AOT/isooctane reversed micelles with complete monomer conversion into the polymer. The resultant polymer exhibits relatively narrow polydispersity, as shown in Table 6.

In this embodiment, the reversed micelles act as three-dimensional templates for the organization of the monomer prior to polymerization.

The reversed micelles are prepared from isooctane and the anionic surfactant AOT. The resultant reversed micelles and the Isooctane are then introduced from reservoirs 10 and 12, respectively, into mixing port 28 through flow controllers 20 and 22, respectively. The contents of mixing port 28 are then introduced into mixing unit 30 and mixed with an enzymatic solution of HRP introduced into mixing unit 30 from reservoir 14 through flow controller 24. The contents of mixing unit 30 are then introduced into mixing unit 32 and mixed with a suitable monomer such as para-ethylphenol introduced into mixing unit 32 from reservoir 16 through flow controller 26. After mixing, the contents of mixing unit 32 are introduced into reactor 34, which is cooled by cooling jacket 44, where polymerization is initiated by the introduction of $H_2O_2$ through flow controller 18 into reactor 14. As the monomers are polymerized, the dense polymers settle to the bottom of the reactor.

After polymerization is complete, the contents of reactor 34 are introduced into centrifuge 36 where the polymer is isolated. The polymer may alternatively be isolated using filters.

After the polymer is isolated, the water in the recycled reaction components is removed by contacting with molecular sieves in dehumidifier 38. Concentrations of water, surfactant, enzyme and monomers are anlyzed in the sampling port 40 and the information is relayed to the feedback controller 42. Based upon this information, the feed back controller communicates with different flow controllers (18, 20, 22, 24 and 26) to adjust the concentrations in the feed to the reactor 34.

Monomers which can be polymerized in reversed micelles include the following phenols, aromatic amines, and mixed functional groups:

| Phenols | Aromatic Amines | Mixed Groups |
| --- | --- | --- |
| 2,6-Dihydroxy-naphthalene | Aniline | p-Hydroxythiophenol |
| p-Ethylphenol | Benzidine | |
| βNaphthol | | |
| p-butylphenol | | |
| 1-Pyrenol | | |

Polymer yields as high as 95% are possible for reactions in reversed micelles and molecular weight can be controlled by controlling the polarity of the oil. Uniformity in size of

TABLE 6

Monomer conversion and polymer molecular weight and dispersity in different reaction media.

| SAMPLE | SYNTHESIS MEDIUM | $M_w$ (p.d.)[1] | COMMENTS |
| --- | --- | --- | --- |
| Poly (p-ethylphenol) | AOT/isooctane reversed micelles | 2,500 (1.4) | 100% monomer conversion to polymer |
| Poly (p-ethylphenol) | 85/15 dioxane/water | 3,400 (>2.0) | Good monomer conversion; poor polymer yield |
| Poly (p-ethylphenol) | Isooctane/buffer biphasic system | 1,700 (>2.0) | Good monomer conversion; fair polymer yield |
| Poly (p-phenylphenol) | 85/15 dioxane/water | 3,000 (>2.0) | Good monomer conversion; fair polymer yield |

[1]Molecular weights were determined with 1% LiBr in DMF as GPC solvent.
p.d. = polydispersity the reverse micelles leads to narrow polydispersity in the resultant polymer.

Figure 9:
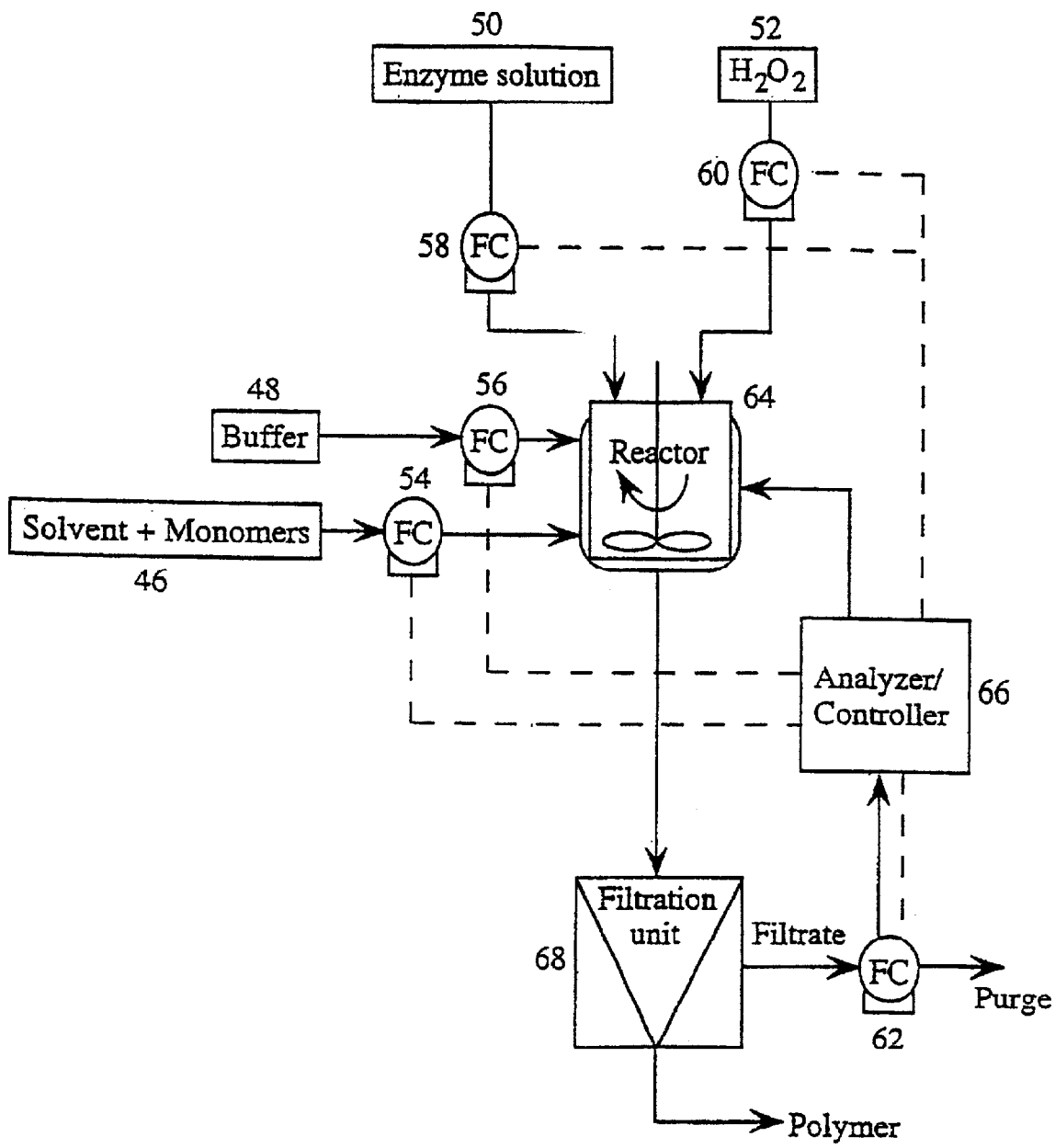
FIG. 9 is a schematic drawing of a preferred embodiment of the invention.

A second preferred embodiment, shown in FIG. 9, includes a monophasic system where the monomer is polymerized in a polar solvent/water mixture such as a dioxane/water mixture where the monomer conversion may be controlled by hydrogen peroxide and HRP. The molecular weight of the polymer may be controlled by adjusting the residence time of the reacting species in the reactor, by molecular weight cutoff filtration, and by the amount of reactants. It is preferable that the ratio of enzyme and hydrogen peroxide is maintained throughout the reaction which can require more than 24 hours for completion. The amount of enzyme and hydrogen peroxide are determined by the amount of monomer.

FIG. 9 is a schematic diagram of enzymatic polyphenol synthesis in an ethanol/water mixture. The polar solvent, monomer, water, hydrogen peroxide, and enzymatic solution are introduced into reactor 64 from their respective reservoirs (46, 48, 50, and 52) through their respective flow controllers (54, 56, 58, and 60), and mixed. After polymerization, the polymer and any post-reaction components (non-consumed reaction components) are run through filtration unit 68, as shown in FIG. 9., to isolate the polymer from the reactants. A centrifuge and/or filters can be used to isolate the polymer. After filtration, the filtrate is introduced into analyzer/controller 66 through flow controller 62 to determine concentration and volume, and then recycled back into reactor 64. Unwanted filtrate is purged through flow controller 62. Fresh reaction components and monomer may then be added to the reactor for continuous production of the polymer.

Suitable polar solvents for use in the monophasic system may include organic solvents such as methanol, ethanol, acetone, tetrahydrofuran, dimethyformamide, isopropyl alcohol, dioxane and dimethylsulfoxide.

Suitable monomers for polymerization in the polar solvent/water mixture include the following phenols, aromatic amines, and mixed functional groups:

| Phenols | Aromatic Amines | Mixed Groups |
| --- | --- | --- |
| Anisole | Aniline | p-Amino m-cresol |
| 1,2-Benzenediol | Benzidine | 2-Hydroxybenzylalcohol |
| p-n-Butylphenol | p-n-Butylaniline | 8-Hydroxyquinoline |
| Cresols (o, m, & p) | p-sec-Butylaniline | p-Hydroxythiophenol |
| 1,3-Dihydroxynaphthalene | 2,6-Diethylaniline | Isoquinoline |
| 1,5-Dihydroxynaphthalene | 3,5-Diethylaniline | 2-Methyl 8-quinolinol |
| 3,4-Dimethylphenol | 2,6-Dimethylaniline | p-Phenylazophenol |
| p-Ethylphenol | 3,5-Dimethylaniline | Tyrosine |
| Methoxyphenol (o & m) | p-Ethylaniline | |
| Naphthol (alpha & beta) | 3-Phenylenediamine | |
| p-n-Octylphenol | p-n-Propylaniline | |
| Phenol | | |
| p-Phenoxyphenol | | |
| Phenylphenol (m & p) | | |
| 3-(3-Phenoxyphenoxy)phenol | | |

Figure 11:
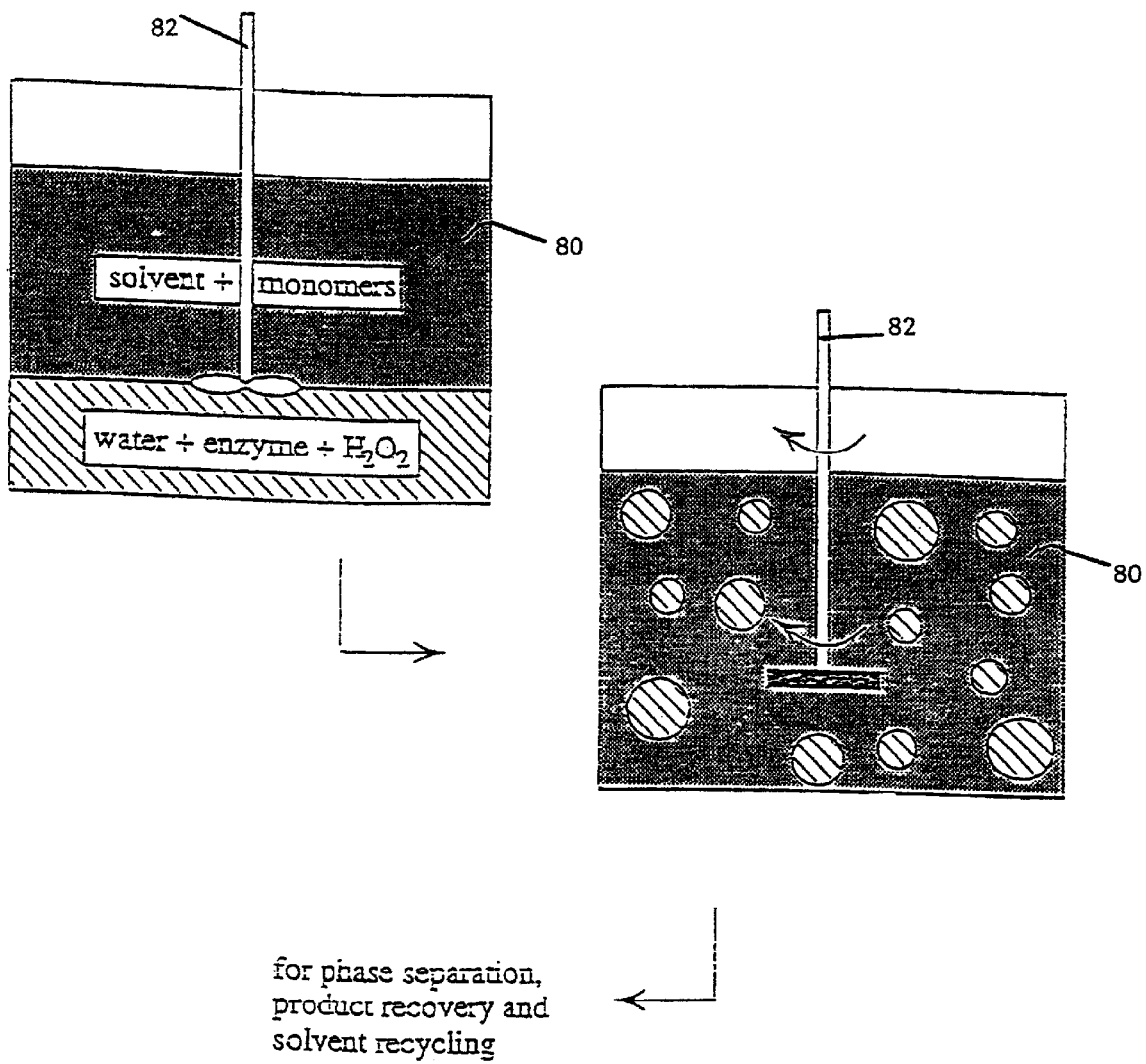
FIG. 11 is a schematic and perspective view of a preferred embodiment of the invention.

A third preferred embodiment of the method, partially shown in FIG. 11, comprises a biphasic system in which water and a water-immiscible organic solvent, such as chloroform or hexane, and a monomer are introduced into stirred tank reactor 80. Upon addition of hydrogen peroxide and enzyme, the reaction takes place at the oil-water interface. The enzyme remains soluble in the aqueous phase while the hydrophobic monomer remains largely in the organic phase. A dynamic macroemulsion is created by vigorous stirring the two phases with stirring device 82. Since no surfactant is involved in creating the emulsion, the product is free from possible surfactant contamination. Following polymerization, the contents of reactor 80 are analyzed and removed for phase separation, product recovery, and solvent recycling as in the above described embodiments.

Figure 10:
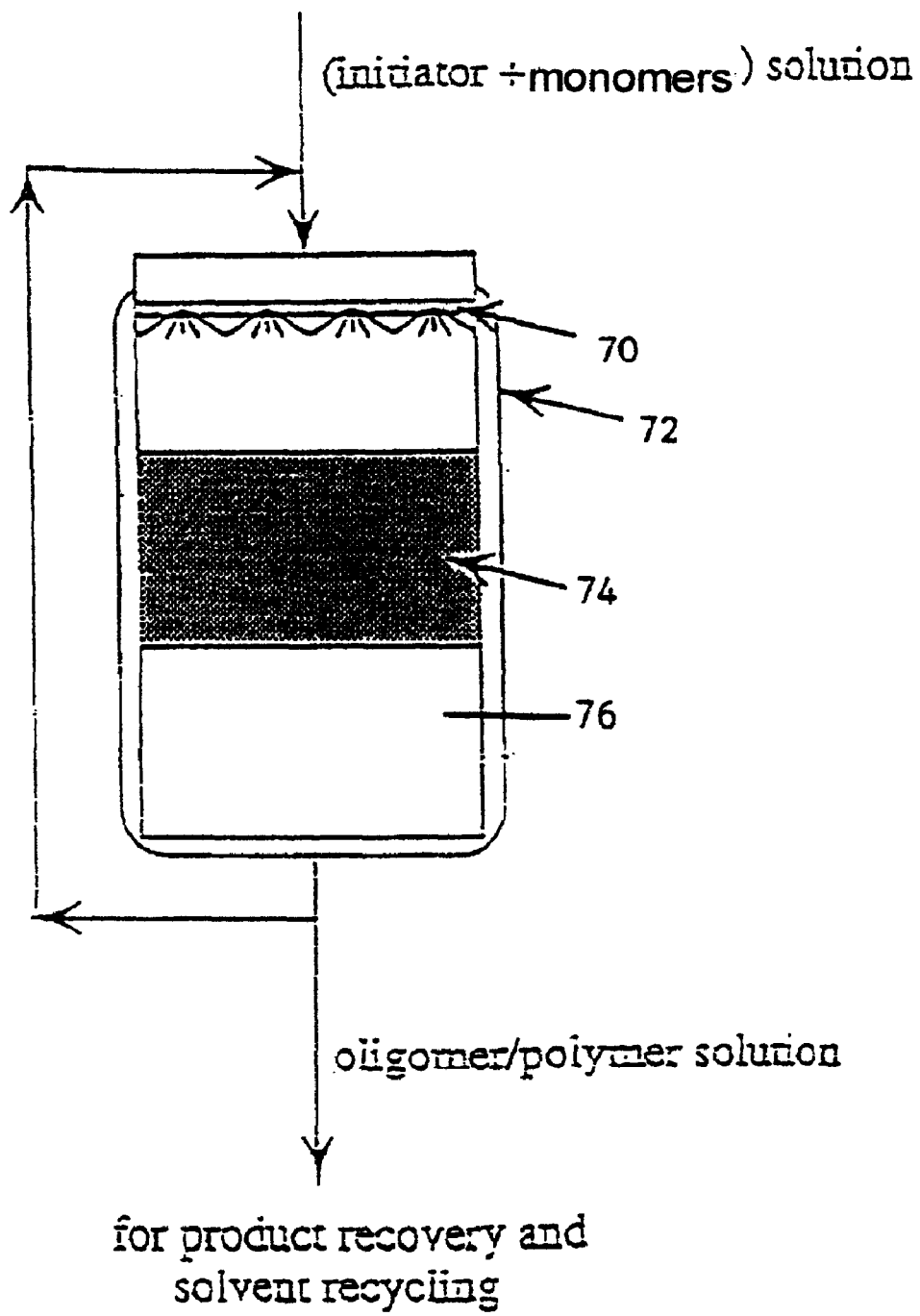
FIG. 10 is a cross-sectional view of the reactor of a preferred embodiment of the invention.

In contrast to the homogenous dispersion of the enzyme in the above described embodiments, the enzyme can also reused by immobilizing the enzyme on an inert support such as silica gel, e.g: retractable enzyme bed 74, as shown in FIG. 10, or on the inside walls of a tube reactor to construct a packed bed reactor or a plug flow reactor. FIG. 10 illustrates an embodiment of packed bed reactor 76 with distribution cap 70 and cooling jacket 72. In this embodiment, the monomer conversion and polymer molecular weight can be controlled by varying the residence time of the monomer. Residence time can be regulated by controlling the flow rate of monomer solution through the enzyme bed. Over time the immobilized enzyme will become contaminated and will require removal for cleaning purposes.

Although specific features of the invention are shown in some drawings and not others, this is for convenience only as some feature may be combined with any or all of the other features in accordance with the invention.

Other embodiments will occur to those skilled in the art and are within the following claims.

What is claimed is:

1. A low cost method for producing polyphenols or polyaromatic amines in large scale comprising the steps of polymerizing a monomer or a mixture of monomers in pre-reaction components in a reactor, wherein polymerization is catalyzed by an oxidizing enzyme, yielding phenolic or aromatic amine polymers, non-consumed reactants, and non-consumed reaction medium, wherein said polymerization is of monomer or mixture of monomers and their products with functional group 'Y' attached to an aromatic ring with a hydroxyl group (—OH) for aromatic phenols or with an amine group (—NH$_2$) for aromatic amines;

and wherein the non-consumed reactants and non-consumed reaction medium together comprise post-reaction components;

dehydrating the reaction medium;

isolating the polymers from the post-reaction components; and recycling at least a portion of the post-reaction components;

wherein rates of reaction are controlled for tailoring molecular weight and dispersity of the polymer by use of sampling ports for monitoring and adjusting reaction conditions, said conditions including temperature, residence time, enzyme activity, water content, and concentrations of consumable and non-consumable reactants;

said polymer molecular weight being in the range of 700 to 22,000;

and said polymer dispersity being close to 1.0.

2. The method of claim 1, wherein said non-consumed reactants include enzyme and remaining monomers, and wherein said non-consumed reaction medium includes a reversed micellar solution comprising water, a solvent and a surfactant.

3. The method of claim 1, wherein said non-consmed reactants include enzyme and remaining monomers, and wherein said non-consumed reaction medium includes a buffer and a water-miscible solvent.

4. The method of claim 1, wherein said non-consumed reactants include enzyme and remaining monomers, and wherein said non-consumed reaction medium includes water.

5. The method of claim 1, wherein said non-consumed reactants include enzyme and remaining monomers and the non-consumed reaction medium includes two phases, wherein said first phase comprises water to dissolve hydrogen peroxide, enzyme and some monomer or mixture of monomers, and said second phase comprises a water-immiscible solvent to dissolve the remaining monomer or mixture of monomers; and said reactor comprising a stirred tank to create a dynamic emulsion.

6. The method of claim 1, wherein said polymer is isolated from said post-reaction components by means of a filtration unit yielding isolated polymers and a filtrate, said filtrate comprising said post-reaction components.

7. The method of claim 1, wherein said polymer is isolated from said post-reaction components by means of a centrifuge yielding isolated polymers and a filtrate, said filtrate comprising said post-reaction components.

8. The method of claim 1, wherein the recycling step includes recycling a solvent.

9. The method of claim 1, wherein the recycling step includes isolating a sample of the post-reaction components by means of a sampling port;

analyzing said sample by an analyzing means to determine concentration and volume levels of the post-reaction components;

recycling said post-reaction components into a mixing unit;

communicating said concentration and said volume levels for said sample by a first communication means from said analyzing means to a feed back controller which determines calculated amounts of monomer or mixture of monomers and pre-reaction components, said amounts of monomer or mixture of monomers and pre-reaction components based on predetermined optimal ratios, to be added to said post-reaction components in said mixing unit, wherein said monomer or mixture of monomers, pre- reaction components and post-reaction components comprise a reaction solution; and introducing said reaction solution into said reactor.

10. The method of claim 3, wherein said enzyme is immobilized on an inert support, said support provided in said reactor.

11. A low cost method for producing polyphenols or polyaromatic amines in large scale comprising the steps of mixing pre-reaction components comprising reversed micelles; an oxidizing enzyme; and hydrogen peroxide in a mixing port;

introducing said pre-reaction components and a monomer or mixture of monomers into a reactor, said monomer selected from the group consisting of 2,6-Dihydroxy-naphthalene p-Ethylphenol p-Naphthol p-butylphenol 1-Pyrenol Aniline Benzidine p-Hydroxythiophenol;

polymerizing said monomer or mixture of monomers in said pre-reaction components in said reactor yielding a phenolic or aromatic amine polymer, non- consumed reactants, and non-consumed reaction medium, wherein said polymerization is of monomer or mixture of monomers and their products with functional group 'Y' attached to an aromatic ring with a hydroxyl group (—OH) for aromatic phenols or with an amine group (—NH$_2$) for aromatic amines; and wherein saiid non-consumed reactants and said non-consumed reaction medium comprise post-reaction components;

wherein rates of reaction are controlled for tailoring molecular weight and dispersity of the polymer by use of sampling ports for monitoring and adjusting reaction conditions, said conditions including temperature, residence time, enzyme activity, water content, and concentrations of consumable and non-consumable reactants; wherein said polymer molecular weight being in the range of 700 to 22,000; and said polymer dispersity being close to 1.0.

isolating said polymer from said post-reaction components by an isolating means;

dehumidifying said post-reaction components by means of molecular sieves;

isolating a smaple of said post-reaction components by means of a sampling port;

analyzing said sample by an analyzing means to determine concentration and volume levels of the post-reaction components;

recycling said post-reaction components into a mixing unit;

communicating said concentration and said volume levels for said sample by a first communication means from said analyzing means to a feed back controller which determines calculated amounts of monomer or mixture of monomers and reaction components, said amounts of monomer or mixture of monomers and reaction components based on predetermined optimal ratios, to be added to said post-reaction components in said mixing unit, wherein said monomer or mixture of monomers, pre-reaction components and post-reaction components comprise a reaction solution; and introducing said reaction solution into said reactor.

12. The method of claim 1, wherein said enzyme is immobilized on an inert support, said support provided in said reactor.

13. The method of claim 1 wherein the reactor comprises a packed bed reactor.

14. The method of claim 1, wherein said reactor comprises a plug flow reactor.

15. A low cost method for producing polyphenols or polyaromatic amines comprising the steps of mixing pre-reaction components: said pre-reaction components comprising a bulk organic solvent mixture; an oxidizing enzyme; water; a surfactant; and hydrogen peroxide in a mixing port;

introducing said reaction components and a monomer or a mixture of monomers into a reactor, said monomer selected from the group consisting of Anisole Aniline p-Amino m-cresol 1,2-Benzenediol Benzidine p-n-Butylphenol p-n-Butylaniline 8-Hydroxyquinoline Cresols (p, m, & p)

p-sec-Butylaniline p-Hydroxythiophenol 1,3-Dihydroxynaphthalene
2,6-Diethylaniline
Isoquinoline
1,5-Dihydroxynaphthalene
3,5-Diethylaniline
2-Methyl 8-quinolinol
3,4-Dimethylphenol
2,6-Dimethylaniline
p-Phenylazophenol
p-Ethylphenol
3,5-Dimethylaniline
Tyrosine
Methoxyphenol (p & m)
p-Ethylaniline
Naphthol (α & β)
3-Phenylenediamine
p-n-Octylphenol
p-n-Propylaniline
Phenol
p-Phenoxyphenol
Phenylphenol (m & p)
3-(3-Phenoxyphenoxy)phenol;

polymerizing said monomer or mixture of monomers in said pre-reaction components in said reactor yielding a phenolic or aromatic amine polymer, non- consumed reactants, and non-consumed reaction medium, wherein said polymerization is of monomer or mixture of monomers and their products with functional group 'Y' attached to an aromatic ring with a hydroxyl group (—OH) for aromatic phenols or with an amine group (—NH$_2$) for aromatic amines; and wherein said non-consumed reactants and said non-consumed reaction medium together are post-reaction components;

wherein rates of reaction are controlled for tailoring molecular weight and dispersity of the polymer by use of sampling ports for monitoring and adjusting reaction conditions, said conditions including temperature, residence time, enzyme activity, water content, and concentrations of consumable and non-consumable reactants; wherein said polymer molecular weight being in the range of 700 to 22,000; and said polymer dispersity being close to 1.0.

introducing said polymer and said post-reaction components into a filtration unit;

isolating said polymer from said post-reaction components by an isolating means;

isolating a sample of said post-reaction components by means of a sampling port;

analyzing said sample by an analyzing means to determine concentration and volume levels of said post-reaction components;

recycling at least a portion of said post-reaction components;

communicating said concentration and said volume levels for said sample by a first communication means from said analyzing means to a feed back controller which determines calculated amounts of monomer or mixture of monomers and reaction components, said amounts of monomer or mixture of monomers and reaction components based on predetermined optimal ratios, to be added to said post-reaction components in said mixing unit, wherein said monomer or mixture of monomers, pre-reaction components and post-reaction components comprise a reaction solution; and introducing said reaction solution into said reactor.

16. The method of claim 15, wherein said enzyme is immobilized on an inert support, said support provided in said reactor.

17. The method of claim 15, wherein the reactor comprises a packed bed reactor.

18. The method of claim 15, wherein said reactor comprises a plug flow reactor.

19. A low cost method for producing polyphenols and polyaromatic amines in large scale comprising the steps of mixing a monomer or mixture of monomers and pre-reaction components in a reactor; wherein said pre-reaction components comprising water, an oxidizing enzyme, hydrogen peroxide, and a water-immiscible organic solvent;

stirring the monomer or mixture of monomers and pre-reaction components in the reactor with a stirring means to create a dynamic macroemulsion;

polymerizing said monomer or mixture of monomers in said pre-reaction components in said reactor yielding a phenolic or aromatic amine polymer, non- consumed reactants, and non-consumed reaction medium, wherein said polymerization is of monomer or mixture of monomers and their products with fuctional group 'Y' attached to an aromatic ring with a hydroxyl group (—OH) for aromatic phenols or with an amine group (—NH$_2$) for aromatic amines; and wherein said non-consumed reactants and said non-consumed reaction medium together are post-reaction components;

wherein rates of reaction are controlled for tailoring molecular weight and dispersity of the polymer by use of sampling ports for monitoring and adjusting reaction conditions, said conditions including temperature, residence time, enzyme activity, water content, and concentrations of consumable and non-consumable reactants; wherein said polymer molecular weight being in the range of 700 to 22,000; and said polymer dispersity being close to 1.0.

introducing said polymer and said post-reaction components into a filtration unit;

isolating said polymer from said post-reaction components by an isolating means provided in said filtration unit;

isolating a sample of said post-reaction components by a means of a sampling port;

analyzing each said sample by an analyzing means to determine concentration and volume levels for said post-reaction components;

recycling at least a portion of said post-reaction components into a mixing unit;

communicating said concentration and said volume levels for said sample by a first communication means from said analyzing means to a feed back controller which determines calculated amounts of monomer or mixture of monomers and reaction components, said amounts of monomer or mixture of monomers and reaction components based on predetermined optimal ratios, to be added to said post-reaction components in said mixing unit, wherein said monomer or mixture of monomers, pre-reaction components and post-reaction components comprise a reaction solution; and introducing said reaction solution back into the reactor.

* * * * *